United States Patent
Lee

(10) Patent No.: US 7,427,519 B2
(45) Date of Patent: Sep. 23, 2008

(54) METHOD OF DETECTING END POINT OF PLASMA ETCHING PROCESS

(75) Inventor: Hong-Ji Lee, Hsinchu (TW)

(73) Assignee: MACRONIX International Co., Ltd., Hsinchu (TW)

( * ) Notice: Subject to any disclaimer, the term of this patent is extended or adjusted under 35 U.S.C. 154(b) by 43 days.

(21) Appl. No.: 11/670,590

(22) Filed: Feb. 2, 2007

(65) Prior Publication Data

US 2008/0186473 A1    Aug. 7, 2008

(51) Int. Cl.
*H01L 21/00*    (2006.01)
*H01L 21/302*    (2006.01)

(52) U.S. Cl. ............... 438/9; 438/9; 438/709; 257/E21.218; 505/411; 216/58; 216/63; 216/67

(58) Field of Classification Search ...... 436/9, 436/709; 257/E21.218; 505/411; 216/58, 216/63, 67
See application file for complete search history.

(56) References Cited

U.S. PATENT DOCUMENTS

2006/0273255 A1* 12/2006 Volkov et al. ............ 250/336.1

2007/0027657 A1* 2/2007 Pinnegar et al. ............ 702/189

* cited by examiner

*Primary Examiner*—Thanh V Pham
(74) *Attorney, Agent, or Firm*—J.C. Patents

(57) ABSTRACT

A method of detecting an end point of a plasma etching process for etching a first layer on a second layer is described, the first layer producing a first etching product and the second layer a second etching product. Time-dependent intensity $[I_{j=1\ to\ m}(t)]$ of a number "m" (m≧1) of spectral line(s) of the first etching product in emission spectrum of the plasma and that $[I_{i=1\ to\ n}(t)]$ of a number "n" (n≧1) of spectral line(s) of the second etching product in the emission spectrum are collected, wherein "m+n≧3" is satisfied. One index of $$Lm(t) = \prod_{i=1, j=1}^{n,m} \frac{I_i(t)}{I_j(t)}, \quad Ls(t) = \sum_{i=1, j=1}^{n,m} \frac{I_i(t)}{I_j(t)},$$

Lm'(t) {=d[Lm(t)]/dt} and Ls'(t) {=d[Ls(t)]/dt} is calculated in real time and plotted with the time. An etching end-point is identified from the plot of the one index with the time.

20 Claims, 2 Drawing Sheets

METHOD OF DETECTING END POINT OF PLASMA ETCHING PROCESS

BACKGROUND OF THE INVENTION

1. Field of the Invention

This invention relates to a method of monitoring a semiconductor process, and more particularly to a method of detecting an end point of a plasma etching process.

2. Description of the Related Art

As the integration degree of semiconductor device is required higher, the control over the plasma etching utilized in the semiconductor process becomes more important. The stop of a plasma etching process may be determined in a time mode, wherein the period of the etching process is fixed to a constant value predetermined based on the experiences. However, since the etching/wafer conditions are rarely constant, a fixed etching period easily causes incomplete etching or too much over-etching.

Another way to determine when to stop a plasma etching process is based on the optical emission spectroscopy (OES) of the plasma. Such a method typically includes monitoring the intensity of one spectral line of one etching product of the layer under the etching target layer in the emission spectrum of the plasma. The time-variation of the intensity reveals when the target layer is etched through to expose the underneath layer, so that a proper end point can be detected for the plasma etching process.

In a modified version of the above method, the intensity of one spectral line of one etching product of the underlying layer and that of one spectral line of one etching product of the target layer are measured and their ratio is calculated in real time. The plot of the ratio with the time shows an enhanced etching-through signal.

However, when there are two or more areas having different etching end-points on a wafer, not all of the end points can be detected with the above methods. FIG. 1 shows the results of respectively applying the two conventional methods of detecting an etching end-point to an exemplary plasma etching process for defining wider holes and narrower holes. The etching process was for simultaneously defining contact holes of 0.16 wide and contact holes of 0.23 μm wide in an inter-layer dielectric (ILD) layer of silicon oxide of 9500 Å thick between an overlying bottom anti-reflection coating (BARC) of 900 Å thick and an etching stop layer of silicon nitride of 200 Å thick. The etching product of silicon nitride being selected was CN, and the spectral line of CN at 387 nm was monitored. The etching product of the silicon oxide being selected was CO, and the spectral line of CO at 483 nm was monitored.

It is known the contact holes of 0.16 μm are opened later than those of 0.23 μm. However, the curve of $I_{387}(t)$ or $I_{387}(t)/L_{483}(t)$ shows only one etching-through signal that allows the etching end-point of the 0.23 μm contact holes to be detected, while the end-point of the 0.16 μm contact holes that is truly important to the plasma etching process cannot be detected because the area percentage of the 0.16 μm contact holes is low.

Therefore, with the conventional end-point detection methods, the degree of the over-etching can be precisely controlled to sustain reasonable consumption of a thin photoresist layer formed in an advance process. Meanwhile, the etching recipe switch timing cannot be well controlled to get a higher selectivity and a better etching profile.

Moreover, as the above end-point detection methods are applied to an etching process for forming contact holes over shallow-junction S/D regions, the etching-through signal is not clear. This makes the end point difficult to detect, so that the Si-loss of the S/D regions cannot be well controlled and the junctions may be damaged.

SUMMARY OF THE INVENTION

In view of the foregoing, this invention provides a method of detecting an end point of a plasma etching process.

The method of this invention is applied to a plasma etching process for etching a first layer on a second layer that includes a material different from that of the first layer, wherein the first layer produces a first etching product and the second layer produces a second etching product. Time-dependent intensity $[I_{j=1\ to\ m}(t)]$ of a number "m" (m≧1) of spectral line(s) of the first etching product in the emission spectrum of the plasma and that $[I_{i=1\ to\ n}(t)]$ of a number "n" (n≧1) of spectral line(s) of the second etching product in the emission spectrum are collected, wherein "m+n≧3" is satisfied. One index of $$Lm(t)\left[=\prod_{i=1,j=1}^{n,m}\frac{I_i(t)}{I_j(t)}\right], Ls(t)\left[=\sum_{i=1,j=1}^{n,m}\frac{I_i(t)}{I_j(t)}\right],$$

Lm'(t) {=d[Lm(t)]/dt} and Ls'(t) {=d[Ls(t)]/dt} is calculated and plotted with the time. At least one etching end-point is then identified from the plot of the one index with the time.

It is also possible to determine at least one end point of the etching process based on two or more Lm(t) [or Ls(t), Lm'(t) or Ls'(t)] curves derived from N (≧2) groups of spectral lines caused by the first and second etching products, wherein the k-th group among the N groups includes a number "m(k)" [m(k)≧1] of spectral line(s) of the first etching product with time-dependent intensity "$I_{k,\ j=1\ to\ m(k)}(t)$" and a number "n(k)" [n(k)≧1] of spectral line(s) of the second etching product with time-dependent intensity "$I_{k,\ i=1\ to\ n(k)}(t)$", and "m(k)+n(k)≧3" is satisfied. After the time-dependent intensities are measured, $$Lm(t)\left[Lm_k(t)=\prod_{i=1,j=1}^{n(k),m(k)}\frac{I_{k,i}(t)}{I_{k,j}(t)}\right], Ls(t)\left[Ls_k(t)=\sum_{i=1,j=1}^{n(k),m(k)}\frac{I_{k,i}(t)}{I_{k,j}(t)}\right],$$

Lm'(t) {$Lm_k'(t)$=d[$Lm_k(t)$]/dt} or Ls'(t) {$Ls_k'(t)$=d[$Ls_k(t)$]/dt} is calculated, in real time, for each group among the N groups and plotted with the time for the identification of at least one etching end point.

Among the four indexes Lm(t), Ls(t), Lm'(t) and Ls'(t), Lm(t) and Lm'(t) are more preferred for magnifying the etching-through response by orders, while Ls(t) and Ls'(t) magnifying the etching-through response by several times. The methods of this invention are particularly useful to the end-point detection of a plasma etching process for forming narrow holes, or for simultaneously forming multiple holes having different etching end-points due to, for example, different widths thereof.

By using the above methods of this invention to an etching process, the etching-through response can be greatly magnified as compared with the prior art, so that the etching end-point is easier to detect. Hence, the degree of an over-etching step can be controlled more precisely to sustain reasonable consumption of a thin photoresist layer. Meanwhile, the timing of switching the etching recipe in a multi-layer etching process can be precisely controlled to get a higher selectivity and a better etching profile.

Furthermore, when this invention is applied to an etching process for forming contact holes over shallow-junction source/drain (S/D) regions, especially S/D regions having relatively shallower junctions in a process of 90 nm or below, the etching end-point is easy to detect. Hence, the Si-loss of the S/D regions can be well controlled, so that the shallow junctions of the same are not damaged.

It is to be understood that both the foregoing general description and the following detailed description are exemplary, and are intended to provide further explanation of the invention as claimed.

DESCRIPTION OF THE PREFERRED EMBODIMENTS

Though the embodiments of this invention only include some cases using Lm(t) curves for etching end-point detection, this invention is also applicable to the cases using Lm'(t) and even the cases using Ls(t) and Ls'(t) respectively. The magnitude of the etching-through response in a Lm'(t) {=d[Lm(t)]/dt} curve is at the same level of that in the corresponding Lm(t) curve. In addition, though Ls(t) or Ls'(t) magnifies the etching-through response by merely several times, they are better than the conventional indexes in the etching end-point detection based on the optical emission spectroscopy (OES) of the plasma.

It is also noted that the selections for the etching product of the etching target layer, the etching product of the underlying layer and the spectral lines of the etching products to be monitored in this invention can be made according to the result of a prior experiment, wherein many Lm(t) [or Lm'(t), Ls(t) or Ls'(t)] curves are plotted for all combinations of two etching products respectively from the two layers and the spectral lines thereof. The combinations making larger etching-through signals are preferred. It is particularly noted that the following combinations for an etching process of a SiO-on-SiN stack are just exemplary but are not intended to limit the scope of this invention.

EXAMPLES

Figure 1:
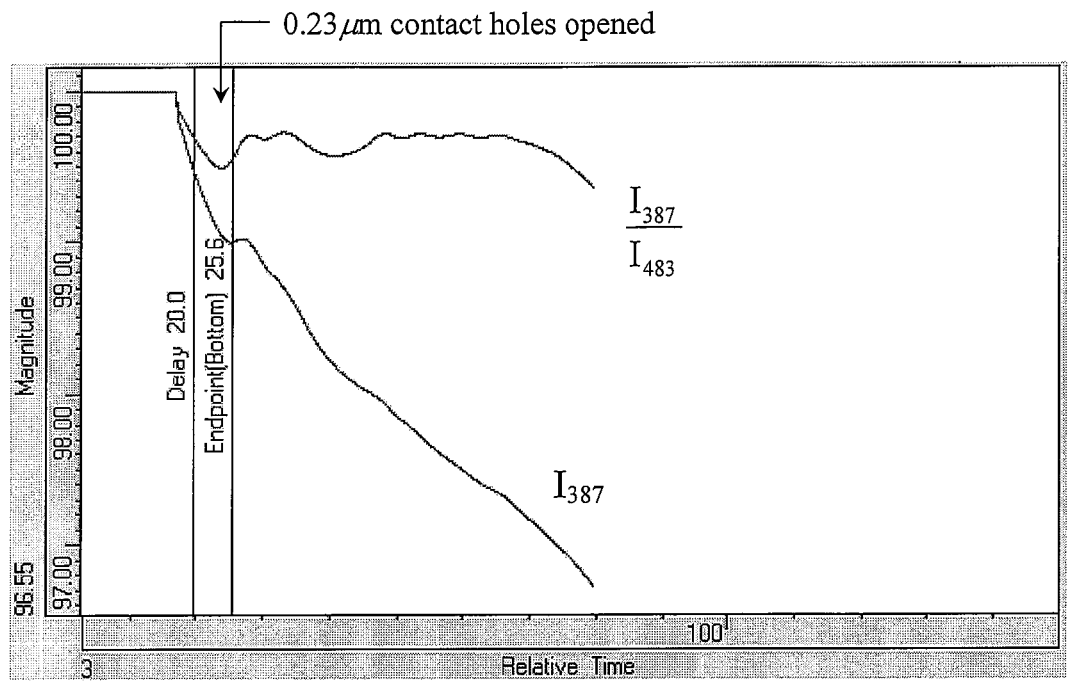
FIG. 1 shows the results of respectively applying two conventional methods of detecting an end point to an exemplary plasma etching process that defines wider holes and narrower holes.
Figure 2:
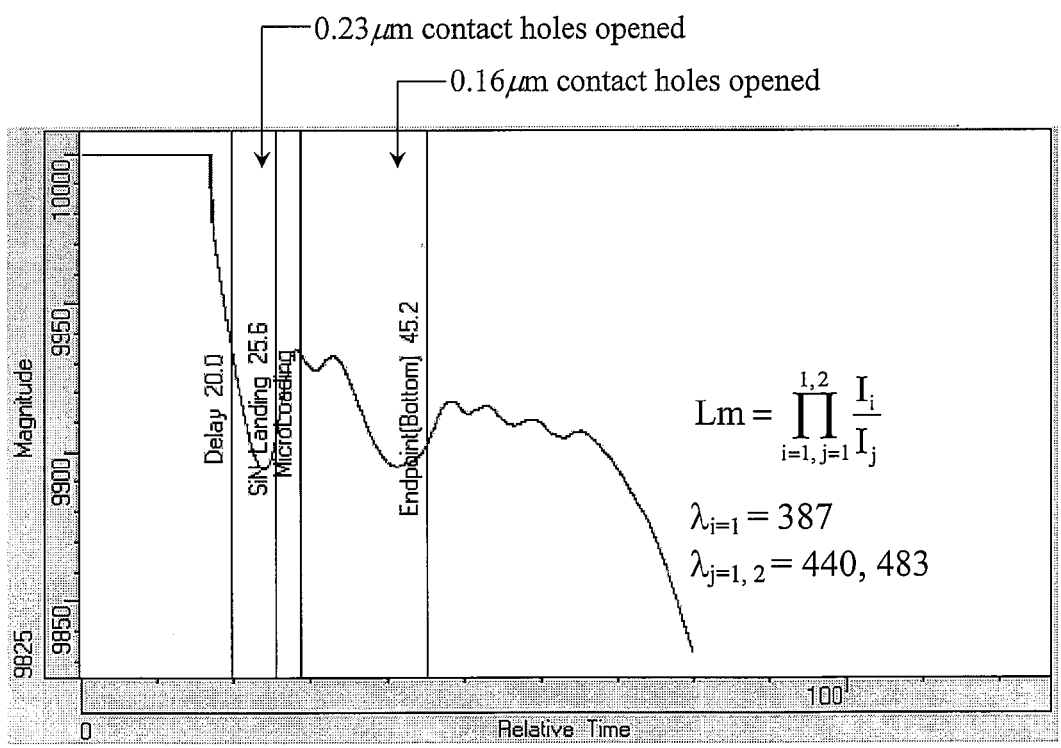
FIGS. 2 and 3 show two Lm(t) curves derived from respective intensities of two groups of spectral lines in the emission spectrum of the plasma in the above exemplary plasma etching process, according to an embodiment of this invention.
Figure 3:
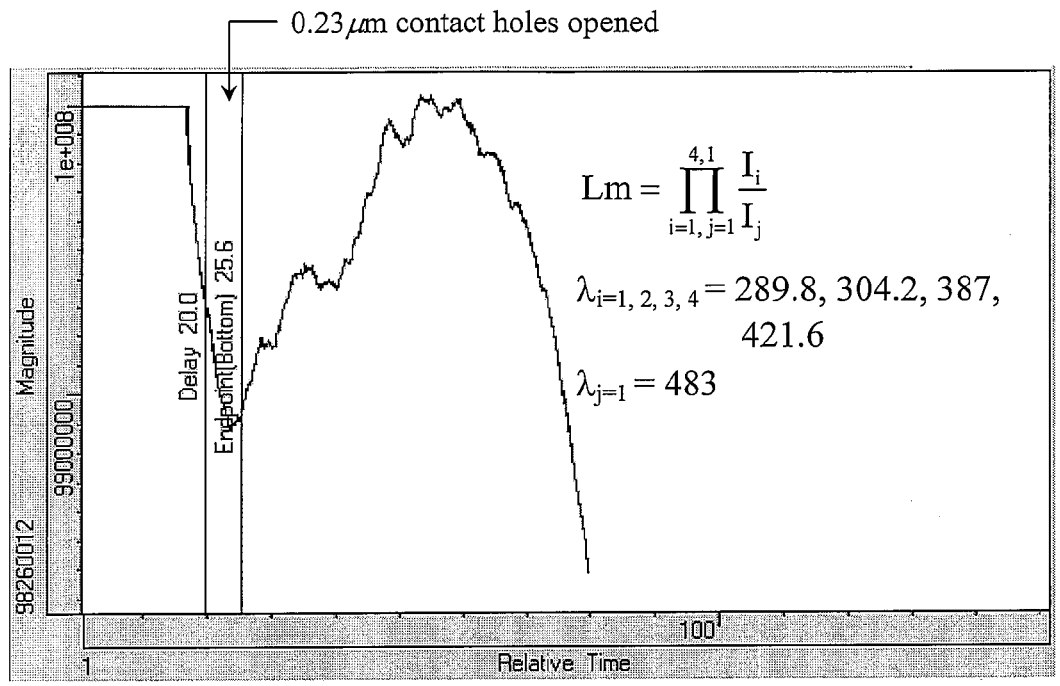

FIGS. 2 and 3 show two Lm(t) curves derived from respective intensities of two groups of spectral lines in the emission spectrum of the plasma in an exemplary plasma etching process as described in the above "Description of the Related Art", according to an embodiment of this invention.

Specifically, the etching process was for simultaneously defining contact holes of 0.16 μm and contact holes of 0.23 μm in an oxide ILD layer of 9500 Å between an overlying BARC of 900 Å and an etching stop layer of silicon nitride of 200 Å.

There are mainly 14 spectral lines of CN in the emission spectrum of the plasma, respectively at 289.3, 304.2, 358.6, 359.0, 386.2, 387, 387.1, 388.3, 418.1, 419.7, 421.6, 585.8, 647.8 and 787.3 (nm). It is also known that CO in the plasma mainly makes 17 spectral lines respectively at 238.9, 269.8, 283.3, 292.5, 302.8, 313.4, 313.8, 325.3, 330.6, 349.3, 451.1, 482.5, 483.5, 519.8, 561.0, 608.0 and 662.0 (nm).

In the case of FIG. 2, one spectral line at 387 nm was selected for CN, and two spectral lines respectively at 440 nm and 483 nm were selected for CO. After respective intensities of the spectral lines were measured, the time-dependent Lm(t) is calculated in real time with the following equation:

$$Lm(t) = \prod_{i=1, j=1}^{1,2} \frac{I_i(t)}{I_j(t)} = \frac{I_{i=1}(t)}{I_{j=1}(t)} \times \frac{I_{i=1}(t)}{I_{j=2}(t)},$$

wherein $I_i$ is the intensity of the spectral line at a wavelength "$\lambda_i$" of CN, $I_j$ is the intensity of the spectral line at a wavelength "$\lambda_j$" of CO, $\lambda_{i=1}$=387 nm, and $\lambda_{j=1, 2}$=0.440 nm, 483 nm.

As shown in FIG. 2, the etching-through signal of the 0.16 μm contact holes is clearly shown, so that the etching end-point of the 0.16 μm contact holes that is truly important to the plasma etching process can be easily detected.

In the case of FIG. 3, four spectral lines respectively at 289.8 nm, 304.2 nm, 387 nm and 421.6 nm were selected for CN, and one spectral line at 483 nm was selected for CO. After respective intensities of the spectral lines were measured, the time-dependent Lm(t) was calculated in real time with the following equation:

$$Lm(t) = \prod_{i=1, j=1}^{4,1} \frac{I_i(t)}{I_j(t)} = \frac{I_{i=1}(t)}{I_{j=1}(t)} \times \frac{I_{i=2}(t)}{I_{j=1}(t)} \times \frac{I_{i=3}(t)}{I_{j=1}(t)} \times \frac{I_{i=4}(t)}{I_{j=1}(t)}$$

wherein $I_i$ is the intensity of the spectral line at a wavelength "$\lambda_i$" of CN, $I_j$ is the intensity of the spectral line at a wavelength "$\lambda_j$" of CO, $\lambda_{i=1, 2, 3, 4}$=289.8 nm, 304.2 nm, 387 nm, 421.6 nm, and $\lambda_{j=1}$=483 nm.

As shown in FIG. 3, the etching-through signal of the 0.23 μm contact holes is magnified, while that of the 0.16 μm contact holes is weakened. It is possible to use this Lm(t) curve in company with the one plotted in FIG. 2 in the detection of the two etching end-points. By doing so, not only the etching-through signal of the 0.23 μm contact holes and that of the 0.16 μm contact holes both can be identified, but also the etching-through signal of the 0.23 μm contact holes is clearer.

A case using the two Lm(t) curves simultaneously corresponds to an above-mentioned case wherein the intensities of the spectral lines of N (=2) groups caused by the first and the second etching products (CO and CN) in the emission spectrum of the plasma are monitored to derive 2 Lm(t) curves, wherein $$Lm_{k=1}(t) = \prod_{i=1,j=1}^{n(k=1)=1, m(k=1)=2} \frac{I_{k=1,i}(t)}{I_{k=1,j}(t)}, \quad Lm_{k=2}(t) = \prod_{i=1,j=1}^{n(k=2)=4, m(k=2)=1} \frac{I_{k=2,i}(t)}{I_{k=2,j}(t)},$$

and "n(k)+m(k)≧3" is satisfied for any value of k. $I_{k,i}$ is the intensity of the spectral line at a wavelength "$\lambda_i$" in the k-th group of spectral lines of CN. $I_{k,j}$ is the intensity of the spectral line at a wavelength "$\lambda_j$" in the k-th group of spectral lines of CO. In the 1$^{st}$ group (k=1) of spectral lines among the two (N=2) groups, $\lambda_{i=1}$=387 and $\lambda_{j=1,2}$=440, 483 (nm). In the 2$^{nd}$ group (k=2) of spectral lines, $\lambda_{i=1,2,3,4}$=289.8, 304.2, 387, 421.6 and $\lambda_{j=1}$=483 (nm).

Accordingly, by applying the method of this invention to an etching process that simultaneously forms wider and narrower holes having different etching end-points, the etching-through response for the narrower ones having a low area percentage (<2%, for example) is not covered by that for the wider ones. Thus, the degree of over-etching can be controlled more precisely to sustain reasonable consumption of a thin photoresist layer, such as a photoresist layer sensitive to ArF excimer laser of 193 nm that is formed in a process of 0.13 μm or below. Meanwhile, the timing of switching the etching recipe in a multi-layer etching process can be precisely controlled to get a higher selectivity and a better etching profile.

Figure 4:
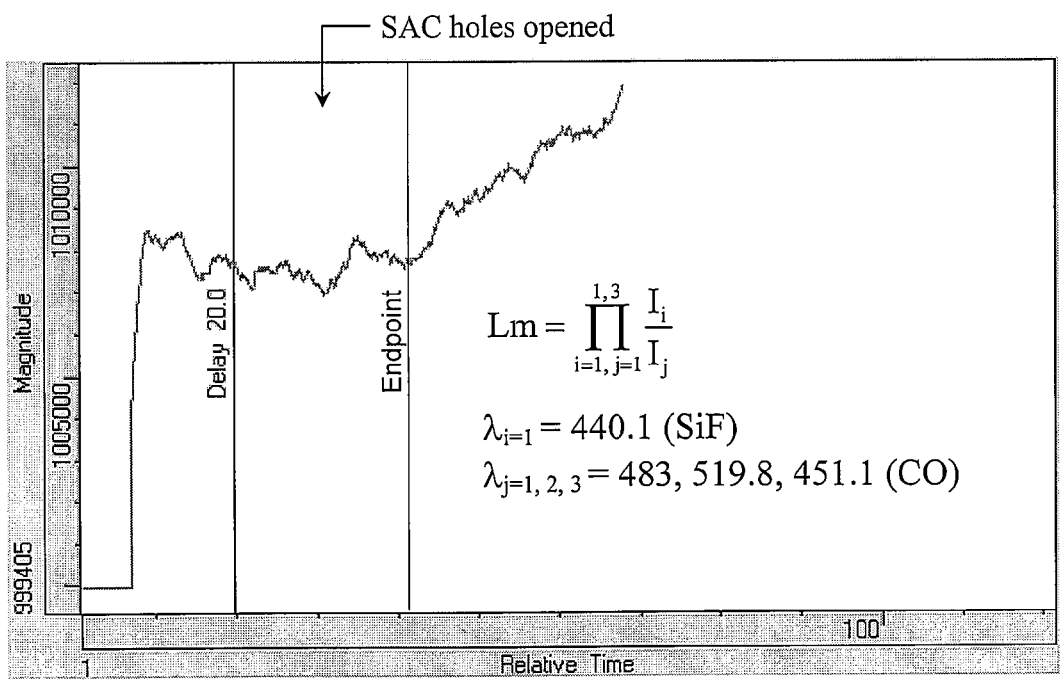
FIG. 4 shows an Lm(t) curve derived from the intensities of certain spectral lines in the emission spectra of the plasma in another exemplary etching process for forming contact holes over S/D regions, according to an embodiment of this invention.

FIG. 4 shows an Lm(t) curve derived from the intensities of certain spectral lines in the emission spectra of the plasma in another exemplary etching process for forming contact holes over S/D regions, according to an embodiment of this invention.

In this example, the etching process is for defining self-aligned contact (SAC) holes of 0.11 μm in an oxide ILD layer of 10000 Å between an overlying BARC of 900 Å and a silicon substrate. The SAC holes are formed over the S/D regions between the gate structures, for the formation of SAC contact plugs.

The spectral line at 440.1 nm is selected for SiF as an etching product of the silicon substrate, and those respectively at 483 nm, 519.8 nm and 451.1 nm n are selected for CO as an etching product of the oxide ILD layer. After respective intensities of the selected spectral lines are measured, the time-dependent Lm(t) is calculated in real time with the following equation:

$$Lm(t) = \prod_{i=1,j=1}^{1,3} \frac{I_i(t)}{I_j(t)} = \frac{I_{i=1}(t)}{I_{j=1}(t)} \times \frac{I_{i=1}(t)}{I_{j=2}(t)} \times \frac{I_{i=1}(t)}{I_{j=3}(t)}$$

wherein $I_i$ is the intensity of the spectral line at a wavelength "$\lambda_i$" of SiF, $I_j$ is the intensity of the spectral line at a wavelength "$\lambda_j$" of CO, $\lambda_{i=1}$=440.1 nm (SiF), and $\lambda_{j=1,2,3}$=483 nm, 519.8 nm, 451.1 nm (CO).

As shown in FIG. 4, an etching-through signal of the SAC holes can be identified in the Lm(t) curve, so that an etching end-point is detected. Accordingly, when this invention is applied to an etching process for forming contact holes over shallow-junction S/D regions, especially S/D regions having relatively shallower junctions in a process of 90 nm or below, an etching end-point can be detected. Therefore, the Si-loss of the shallow-junction S/D regions can be precisely controlled, so that the shallow junctions are not damaged.

Accordingly, the etching end-point detecting method of this invention is capable of detecting an etching end-point that is difficult to detect in the prior art. Therefore, by utilizing this invention, the degree of over-etching can be controlled more precisely to sustain reasonable consumption of a thin photoresist layer. Meanwhile, the timing of switching the etching recipe can be well controlled to get a higher etching selectivity and a better etching profile.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. A method of detecting an end point of a plasma etching process for etching a first layer on a second layer that comprises a material different from that of the first layer, wherein the first layer produces a first etching product and the second layer produces a second etching product, the method comprising:

collecting time-dependent intensity [$I_{j=1\ to\ m}(t)$] of a number "m" (m≧1) of spectral line(s) of the first etching product in an emission spectrum of the plasma and time-dependent intensity [$I_{i=1\ to\ n}(t)$] of a number "n" (n≧1) of spectral line(s) of the second etching product in the emission spectrum, wherein "m+n≧3" is satisfied;

calculating, in real time, one index of $$Lm(t) = \prod_{i=1,j=1}^{n,m} \frac{I_i(t)}{I_j(t)}, \quad Ls(t) = \sum_{i=1,j=1}^{n,m} \frac{I_i(t)}{I_j(t)},$$

Lm'(t) {=d[Lm(t)]/dt} and Ls'(t) {=d[Ls(t)]/dt} and plotting the same with the time; and identifying at least one etching end-point from the plot of the one index with the time.

2. The method of claim 1, wherein the one index is Lm(t) or Lm'(t).

3. The method of claim 1, wherein the plasma etching process is for forming multiple holes having different etching end-points.

4. The method of claim 3, wherein the holes have different widths and thus have the different etching end-points.

5. The method of claim 1, wherein the second layer is an etching stop layer.

6. The method of claim 5, wherein the first and the second layers both are dielectric layers.

7. The method of claim 6, wherein the plasma etching process is for forming contact holes in the first layer.

8. The method of claim 7, wherein the contact holes have the same width or include at least two groups of holes wherein each group of holes has a different width.

9. The method of claim 5, wherein the first layer comprises silicon oxide and the second layer comprises silicon nitride.

10. The method of claim 9, wherein the first etching product is CO and the second etching product is CN.

11. The method of claim 1, wherein the first layer is a dielectric layer, and the second layer is a silicon substrate.

12. The method of claim 11, wherein the plasma etching process is for forming self-aligned contact (SAC) holes in the first layer.

13. The method of claim 11, wherein the second etching product is SiF.

14. A method of detecting an end point of a plasma etching process for etching a first layer on a second layer comprising a material different from that of the first layer, wherein the first layer produces a first etching product and the second layer produces a second etching product, the method comprising:

collecting respective time-dependent intensities of spectral lines of N ($\geq 2$) groups caused by the first and the second etching products in an emission spectrum of the plasma, wherein the k-th group among the N groups includes a number "m(k)" [m(k)$\geq$1] of spectral line(s) of the first etching product having intensity "$I_{k, j=1 \text{ to } m(k)}(t)$" and a number "n(k)" [n(k)$\geq$1] of spectral line(s) of the second etching product having intensity "$I_{k, i=1 \text{ to } n(k)}(t)$", and "m(k)+n(k)$\geq$3" is satisfied;

calculating, in real time, one index of $$Lm(t)\left[Lm_k(t) = \prod_{i=1,j=1}^{n(k),m(k)} \frac{I_{k,i}(t)}{I_{k,j}(t)}\right], Ls(t)\left[Ls_k(t) = \sum_{i=1,j=1}^{n(k),m(k)} \frac{I_{k,i}(t)}{I_{k,j}(t)}\right],$$

$Lm'(t)$ {$Lm_k'(t)=d[Lm_k(t)]/dt$} and $Ls'(t)$ {$Ls_k'(t)=d[Ls_k(t)]/dt$} for each group among the N groups and plotting the same with the time; and identifying at least one etching end point from the plots of the one index with the time respectively for the N groups.

15. The method of claim 14, wherein the one index $Lm(t)$ or $Lm'(t)$.

16. The method of claim 14, wherein the plasma etching process is for forming multiple holes having different etching end-points.

17. The method of claim 16, wherein the holes have different widths and thus have the different etching end-points.

18. The method of claim 17, wherein the first and second layers both are dielectric layers, the second layer is an etching stop layer, and the two holes are contact holes.

19. The method of claim 18, wherein the first layer comprises silicon oxide and the second layer comprises silicon nitride.

20. The method of claim 19, wherein the first etching product is CO and the second etching product is CN.

* * * * *